US012339246B2

(12) United States Patent
Rolandi et al.

(10) Patent No.: US 12,339,246 B2
(45) Date of Patent: Jun. 24, 2025

(54) BIOMIMETIC LEAF WETNESS SENSOR AND METHOD OF MANUFACTURE OF THE SAME

(71) Applicant: The Regents of the University of California, Oakland, CA (US)

(72) Inventors: Marco Rolandi, Santa Cruz, CA (US); Brian Nguyen, Santa Cruz, CA (US)

(73) Assignee: The Regents of the University of California, Oakland, CA (US)

( * ) Notice: Subject to any disclaimer, the term of this patent is extended or adjusted under 35 U.S.C. 154(b) by 216 days.

(21) Appl. No.: 18/201,886

(22) Filed: May 25, 2023

(65) Prior Publication Data

US 2023/0384254 A1 Nov. 30, 2023

Related U.S. Application Data

(60) Provisional application No. 63/345,574, filed on May 25, 2022.

(51) Int. Cl.
*G01N 27/22* (2006.01)
*H01L 21/02* (2006.01)
*H01L 23/38* (2006.01)

(52) U.S. Cl.
CPC ....... *G01N 27/223* (2013.01); *H01L 21/0212* (2013.01); *H01L 23/38* (2013.01)

(58) Field of Classification Search
CPC ............... G01N 27/223; G01N 27/226; G01N 33/0098; H01L 21/0212; H01L 23/38
USPC ......................................... 324/664, 658, 686
See application file for complete search history.

(56) References Cited

U.S. PATENT DOCUMENTS

| 5,334,942 A | * | 8/1994 | Hulse | G01N 27/048 |
| | | | | 324/692 |
| 2020/0116694 A1 | * | 4/2020 | Rinaldi | G01N 27/125 |

FOREIGN PATENT DOCUMENTS

| CN | 110274937 A | * | 9/2019 | .......... G01N 27/223 |
| CN | 110470703 A | * | 11/2019 | .......... G01N 27/223 |
| KR | 101646048 B1 | * | 8/2016 | ........ G01N 33/0098 |
| WO | WO-2019023712 A1 | * | 1/2019 | ............. C09K 11/02 |
| WO | WO-2019077417 A1 | * | 4/2019 | .......... A01G 25/167 |

OTHER PUBLICATIONS

Sarkozi "New standards to curb the global spread of plant pests and diseases" (2019).
Magarey, R.D., et al., "Simulation of surface wetness with a water budget and energy balance approach", Agricultural and Forest Meteorology 139 (2006) 373-381.
Sentelhas, P.C., et al., "Suitability of relative humidity as an estimator of leaf wetness duration," Agricultural and Forest Meteorology 148 (2008) 392-400.
Sentelhas, P.C., et al., "Evaluation of a Penman-Monteith approach to provide "reference" and crop canopy leaf wetness duration estimates", Agricultural and Forest Meteorology 141 (2006) 105-117.

(Continued)

*Primary Examiner* — Tung X Nguyen
*Assistant Examiner* — Robert P Alejnikov, Jr.
(74) *Attorney, Agent, or Firm* — Carter, DeLuca & Farrell LLP (57) ABSTRACT

A biomimetic leaf wetness sensor includes a capacitive sensor and a non-conductive polymer layer disposed over the capacitive sensor. The layer includes a replica molded surface corresponding to a plant leaf.

12 Claims, 5 Drawing Sheets

(56) References Cited

OTHER PUBLICATIONS

Kim, K.S., et al., "Model to Enhance Site-Specific Estimation of Leaf Wetness Duration", Plant Disease (2002), 179-185.
Sentelhas, P.C., et al., "Operational exposure of leaf wetness sensors", Agricultural and Forest Meteorology 126 (2004) 59-72.
Li, X.B., et al., "Design of Multi-Channel Fringing Electric Field Sensors for Imaging Part I: General Design Principles", Confeence Record of the 2004 IEEE International Symposium on Electrical Insulation (2004) 19-22.
Huang, Y., et al., "Optimization of the coplanar interdigital capacitive sensor", 43rd Annual Review of Progress in Quantitative Nondestructive Evaluation, vol. 36 (2017) 110017-1-110017-9.
MeterGroup Phytos 31 Manual (2021) pp. 1-17.
Sentelhas, P.C., et al., "Leaf wetness duration measurement: comparison of cylindrical and flat plate sensors under different field conditons", Int J Biometeorol (2007) 51:265-273.
Patle, K.S., et al., "IoT Enabled, Leaf Wetness Sensor on the Flexible Substrates for In-Situ Plant Disease Management", IEEE Sensors Journal, vol. 21, No. 17, Sep. 1, 2021, pp. 19481-19491.
Rowlandson, T., et al., "Reconsidering Leaf Wetness Duration Determination for Plant Disease Management", Plant Disease, 99(3), Mar. 2015, 310-319.
Wang, H., et al., "The Wetting of Leaf Surfaces and Its Ecological Significances", Wetting and Wettability (2015) pp. 295-321.

* cited by examiner

BIOMIMETIC LEAF WETNESS SENSOR AND METHOD OF MANUFACTURE OF THE SAME

CROSS-REFERENCE TO RELATED APPLICATION

The present application claims the benefit of and priority to U.S. Provisional Application No. 63/345,574, filed on May 25, 2022. The entire contents of the foregoing application are incorporated by reference herein.

BACKGROUND

Plant diseases cause hundreds of billions of dollars in global crop production each year. Many plant diseases develop when pathogens germinate and proliferate in the fertile environment of excess water collected on leaf surfaces. Accurate measurement of how long a leaf stays wet is an important parameter in assessing the risk of pathogen infestation and deciding on appropriate responses. Commercial leaf wetness sensors (LWS) estimate the duration of leaf wetness by monitoring the water accumulated on the sensor surface. However, this one-size-fits-all sensor surface does not replicate the wetting behavior of specific leaves resulting in an imprecise measurement of leaf wetness.

Plant diseases cause an estimated 19% annual loss of crop production, at an annual cost of hundreds of billions of dollars. Plant diseases on wild and agricultural species are favored by excess water collecting on leaf surfaces, which provides pathogens with the environmental conditions needed to germinate and infect the host plant. The longer a leaf stays wet, the higher the risk that disease will develop, because many plant pathogen propagules require several hours of continuous moisture to germinate and initiate infection. For this reason, estimates of how long leaves stay wet after precipitation or irrigation also known as leaf wetness duration (LWD) is an important component of many disease forecasting systems that allow for effective integrated pest management. Such disease forecasting systems provide growers with guidance about the likelihood of development of specific diseases on particular crops. The forecasts are used in planning appropriate management actions (e.g., agrochemical application) when needed to avoid crop loss, while also unnecessary agrochemical applications that are environmentally and economically costly. Commercially available LWSs commonly use changes in resistance or capacitance to measure the amount and duration of wetness that accumulates on a sensor surface. However, existing sensors estimate leaf wetness duration from one-size-fits-all sensors of a particular shape, texture, and hydrophobicity; these traits strongly affect surface wettability and vary widely among plant species.

Conventional LWSs only measure the presence of water on its surface, which reflects only wetness on a particular surface of moderate wettability and is unable to effectively represent wetness of leaves of actual plants which vary tremendously. Leaf wettability can be described as the leaf's surface's affinity to water and varies based on the chemical composition and structure of leaf surfaces of the plant species. Accurately measuring LWD poses a significant challenge to correctly estimating the risk of fungal disease infections. Current commercially available LWSs are unable mimic the surface of a leaf, so wetness measurements are not directly correlated with what truly occurs on a leaf surface.

Leaf wetness sensors able to measure leaf wetness duration as actually experienced on leaves of diverse plant species would open novel opportunities for field-based research on the ecophysiology of plant-pathogen interactions and help improve disease forecasting systems.

SUMMARY

The present disclosure provides an LWS with replica molded surfaces that closely mimic the leaf of interest and provide a more accurate measurement of leaf wetness duration compared to commercial sensors. This approach allows for better prediction of leaf wetness duration for each plant species, affording individualized and more effective disease forecasting for the management of plant diseases.

The surface structure and surface chemistry of a leaf affects its wettability (hydrophilicity), which may be quantified using a contact angle ($\theta$) of a water droplet on the surface. For example, micro-scale papillae covered with nano-scale wax crystals in the lotus leaf (*Nelumbro nucifera*) make it super-hydrophobic with a contact angle greater than 160°. Such superhydrophobicity gives the leaf self-cleaning properties that has attracted attention as the subject of biomimicry and bioinspiration for engineering of superhydrophobic self-cleaning surfaces. The present disclosure provides a variety of replica molding strategies, which may be used to reproduce the hydrophobic or hydrophilic surfaces of leaves, including both microscale and nanoscale features. Suitable techniques include nickel electro-forming and UV-nanoimprint lithography; sol-gel, soft lithography, and hydrothermal imprinting; and hybrid soft lithography with polydimethylsiloxane combined with polycaprolactone (PCL) and polyurethane acrylate (PUA).

The LWS according to the present disclosure includes an interdigital capacitive sensor insulated with a bio-mimetic polydimethylsiloxane (PDMS) surface. A multi-step molding process is used to replicate the complex surface topography of leaves and integrate it into a capacitive wetness sensor. In embodiments, the interdigital capacitive sensor may be overlaid with two layers of polydimethylsiloxane (PDMS). The first layer acts as an insulating layer for the exposed conductive traces of the interdigital capacitive sensor. The first layer also provides insulation between the capacitive sensor and the outside atmosphere avoiding shorting of the interdigital electrodes by the accumulated water. The second layer of PDMS is a replicative patterned layer and acts as the interface for water droplets and the capacitive sensor. Thus, the second layer of PDMS is a replica of a leaf of a plant species of interest that gives the sensor surface the same wettability as the leaf. Fabrication of the patterned layer may be performed using a two-part casting method where a negative cast of the leaf acts as a stamp which is subsequently pressed into the sensor producing the positive replica of the leaf surface. The present disclosure uses a double-casting method to form a LWS which captures complex leaf surface topography. Therefore, by creating a biomimetic surface, the resulting wettability of the LWS closely matches that of the corresponding leaves.

The LWS estimates leaf wetness duration that is reflective of the wetness of real leaves. This is due to the LWS replicating surface properties of leaves, which addresses the issues associated with commercially available LWSs. The present disclosure also includes examples of LWS manufactured with replica of leaves from three different woody plants with different leaf-wetting properties, including California bay (*Umbellularia californica*), western sycamore (*Platanus racemosa*), and a horticultural variety of *Escallonia* (*Escallonia* x Iveyi). The performance of the LWS based on leaves of these plants were compared with a commercially available sensor (PHYTOS 31; Meter Group, USA) and the results demonstrate that the presently disclosed biomimetic LWSs provide more accurate, species-specific measurements of the leaf wetness duration of plants over a broad range of leaf traits.

According to one embodiment of the present disclosure, a biomimetic leaf wetness sensor is disclosed. The leaf sensor includes a capacitive sensor and a non-conductive polymer layer disposed over the capacitive sensor. The layer includes a replica molded surface corresponding to a plant leaf.

Implementations of the above embodiment may include one or more of the following features. According to one aspect of the above embodiment, the capacitive sensor may include a substrate; a first interdigital electrode having a plurality of first digits disposed on the substrate; and a second interdigital electrode having a plurality of second digits disposed on the substrate, where the plurality of first digits and the plurality of second digits are interdigitated. Each digit of the plurality of first digits and the plurality of second digits may have a width from about 500 μm to about 1,500 μm. The plurality of first digits and the plurality of second digits may be separated by a gap from about 250 μm to about 1500 μm. The non-conductive polymer layer may have a thickness from about 100 μm to about 300 μm. The non-conductive polymer layer may be treated with an oxygen plasma to increase hydrophilicity. The non-conductive polymer layer may be formed from polydimethylsiloxane. The replica molded surface may be formed by placing a replica mold of the plant leaf onto the non-conductive polymer layer during curing thereof.

According to another embodiment of the present disclosure, a method for fabricating a biomimetic leaf wetness sensor is disclosed. The method includes forming a negative mold of a plant leaf. The method also includes coating a capacitive sensor with a non-conductive polymer layer. The method further includes placing the negative mold onto the non-conductive polymer layer to form a replica molded surface corresponding to the plant leaf during curing of the non-conductive polymer layer.

Implementations of the above embodiment may include one or more of the following features. According to one aspect of the above embodiment, the method may include treating the negative mold with a fluorinated trichlorosilane to minimize adhesion with the non-conductive polymer layer. The non-conductive polymer layer may have a thickness from about 100 μm to about 300 μm. The method may also include treating the non-conductive polymer layer with an oxygen plasma to increase hydrophilicity. The non-conductive polymer layer may be formed from polysiloxane. The capacitive sensor may include: a substrate; a first interdigital electrode having a plurality of first digits disposed on the substrate; and a second interdigital electrode having a plurality of second digits disposed on the substrate, where the plurality of first digits and the plurality of second digits are interdigitated. Each digit of the plurality of first digits and the plurality of second digits may have a width from about 500 μm to about 1,500 μm. The plurality of first digits and the plurality of second digits may be separated by a gap from about 250 μm to about 1500 μm.

According to a further embodiment of the present disclosure, a biomimetic leaf sensor is disclosed. The biomimetic leaf wetness sensor includes an interdigital capacitive sensor and a polysiloxane layer disposed over the capacitive sensor. The layer includes a replica molded surface corresponding to a plant leaf.

Implementations of the above embodiment may include one or more of the following features. According to one aspect of the above embodiment, the polysiloxane layer may have a thickness from about 100 μm to about 300 μm. The polysiloxane layer may be treated with an oxygen plasma to increase hydrophilicity. The replica molded surface may be formed by placing a replica mold of the plant leaf onto the non-conductive polymer layer during curing thereof.

BRIEF DESCRIPTION OF DRAWINGS

Various embodiments of the present disclosure are described herein below with reference to the figures wherein.

DETAILED DESCRIPTION

Figure 1:
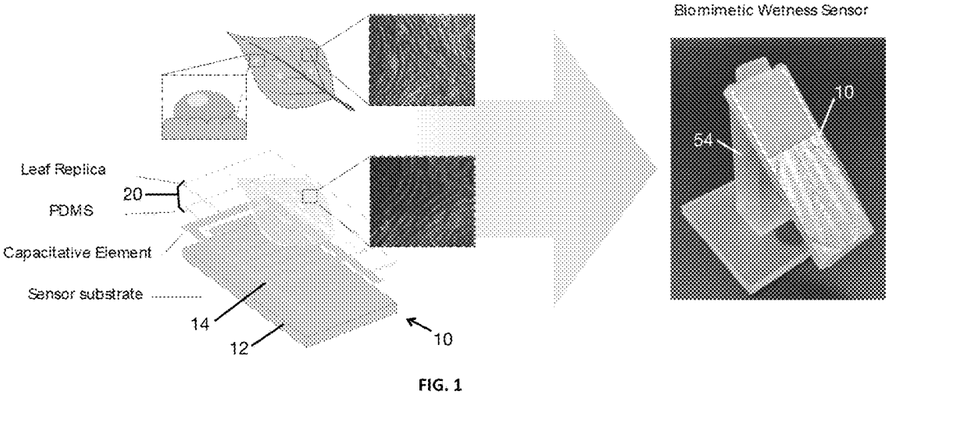
FIG. 1 is a schematic diagram of a biomimetic leaf wetness sensor (LWS) according to an embodiment of the present disclosure.

With reference to FIG. 1, a biomimetic LWS 10 is formed on a printed circuit board (PCB) having a non-conductive substrate 12, which may be rigid or flexible and may have a thickness from about 0.5 mm to about 2 mm. Suitable rigid substrate materials include, but are not limited to, phenolic resin, fiberglass, and the like. Suitable flexible substrate materials include, but are not limited to, polyester (PET), polyimide (PI), polyethylene naphthalate (PEN), polyetherimide (PEI), fluropolymers (FEP), and the like.

Figure 2A:
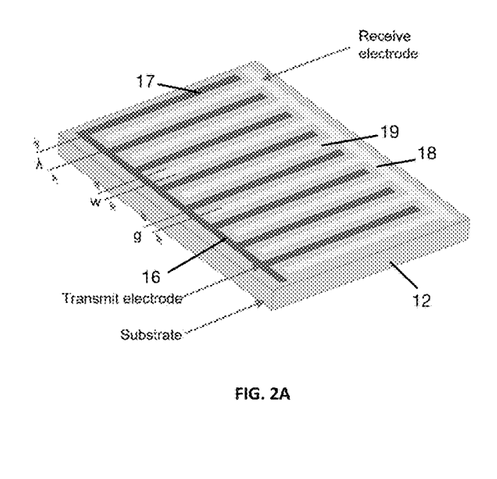
FIG. 2A is a perspective view of the LWS of FIG. 1.

The LWS 10 also includes a capacitive sensor 14 disposed on the substrate 12, which includes a pair of opposing interdigital electrodes 16 and 18 as shown in FIG. 2A. The electrode 16 is a transmit electrode whereas the interdigital electrode 18 is a receive electrode. Each of the electrodes 16 and 18 includes a plurality of interdigitated digits 17 and 19, respectively. The digits 17 and 19 may have a width w from about 500 μm to about 1,500 μm, which in embodiments, may be about 1,000 and may be separated by a gap g of from about 250 μm to about 1500 μm, which in embodiments may be 800 μm. An electrode width-to-gap space ratio (w/g) may be from about 1:1 to about 4:1. The electrodes 16 and 18 may be printed on the substrate 12 using any suitable PCB printing methodology.

Figure 2B:
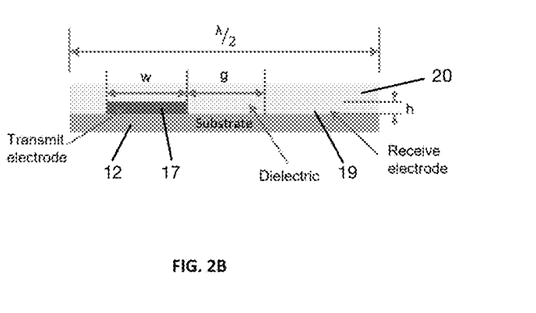
FIG. 2B is a side, cross-sectional view of the LWS of FIG. 1.

With reference to FIGS. 2A and 2B, geometrical parameters including the width of the electrode digits 17 and 19, w, thickness of each electrode digit, h, number of electrode digits, N, and the gap size between them, g, may be adjusted to achieve penetration depth of the fringing field and sensitivity of the sensor. The fringe electric field extends from the electrodes 16 and 18 where electrical environment changes from the formation of water droplets, result in an increase in capacitance. The performance of the sensor is determined by the penetration depth of its fringing field and its sensitivity which, in turn, are dependent on the geometry and material properties of the sensor components. An interdigital electrode structure of the electrodes 16 and 18 arranged in a mutual-capacitance configuration maximizes the contribution of the fringe field effect in sensor capacitance. The capacitive sensor design of the present disclosure achieves an optimum balance between sensor's sensitivity and its penetration depth. In addition, sensor performance is also optimized based on the digit w/g ratio and the number of digits 17 and 19. Increasing the gap space between the digits 17 and 19 yields a greater penetration depth of the fringing field but also results in a loss in sensitivity. Conversely, decreasing the gap space increases the sensor's sensitivity but in-trade loses penetration depth.

The optimal sensor geometry also depends on a thickness of a non-conductive, dielectric surface layer 20 disposed over the capacitive sensor 14 so that the fringe fields extending from the interdigital electrodes can penetrate the insulating polymer while still maintaining adequate sensitivity. The layer 20 may be formed from any suitable polymer such as polysiloxanes, including polydimethylsiloxane (PDMS). The layer 20 may have a thickness from about 100 μm to about 300 μm, which in embodiments may be about 200 μm. The layer 20 may be formed of two layers, a first protective layer may be formed and cured prior to applying a second layer of an uncured polymer that is deposited onto the capacitive sensor 14. The first layer may have a thickness of about 25 μm and may be applied using spin coating at approximately 1,000 revolutions per minute (RPM) for approximately 10 minutes. The polymer may be applied in an uncured state. A pre-polymer (base) and cross-linker (curing agent) mixture may be used, having a ratio of the base to the curing agent of from about 10:1 to about 20:1. The polymer may be cured at a temperature of about 60° C. for approximately 24-48 hours. The second layer is applied in an uncured state and is cured with a negative mold of a surface replica of a leaf as is described below with respect to FIG. 3. The second layer may be applied using spin coating at approximately 250 RPM for approximately 60 seconds to achieve the desired thickness for the layer 20.

During a second stage a surface replica of a leaf is formed on the layer 20, which may be done by pressing a negative mold 90 of the leaf onto the uncured second layer of the layer 20 and then curing the same. The leaf surface being replicated may be of any leafy plant where the LWS 10 is going to be monitoring leaf wetness. The outer layer 24 may be formed by taking a mold of the leaf. In embodiments, other techniques for forming the outer layer 24, including 3D scanning, depth mapping, or other methods for capturing the surface topology of the leaf and then fabricating the mold and/or the layer 20 directly using additive or subtractive manufacturing techniques.

Figure 3:
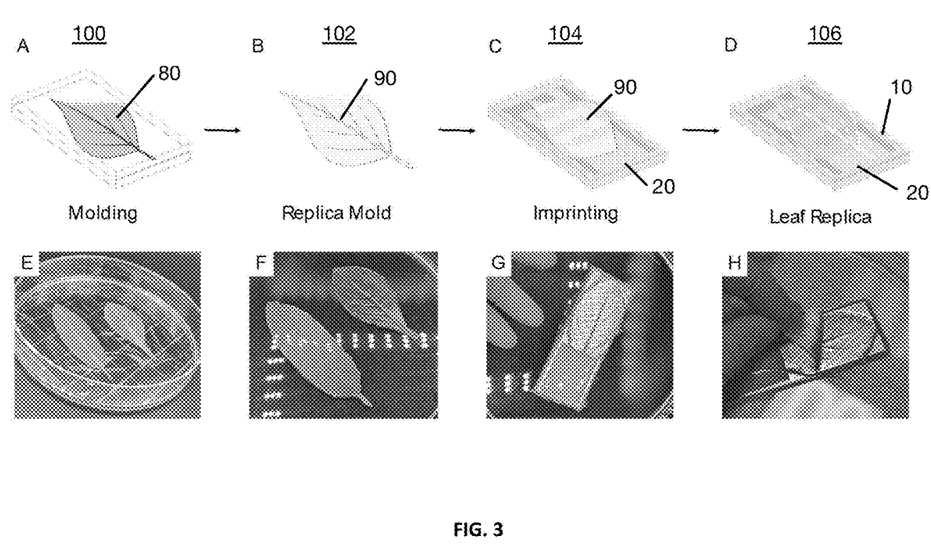
FIG. 3 is a schematic diagram with accompanying photographs of a method for fabricating the LWS according to an embodiment of the present disclosure.

With reference to FIG. 3, which shows a method for fabricating the LWS 10, at step 100, a surface of a leaf 80 is replicated to form a surface replica of the leaf 80 having the same or substantially the same surface features and wettability as the leaf 80. A double casting method may be used for this purpose with the chosen polymer (e.g., PDMS), which includes forming a negative mold 90 by covering the leaf 80 of interested with uncured polymer while the leaf 80 is attached to the bottom of a mold dish (e.g., using double-sided tape), which collects the excess polymer as shown in slides A and E of FIG. 3. In embodiments, where the polymer is PDMS, it is applied in an uncured state. A pre-polymer (base) and cross-linker (curing agent) mixture may be used, having a ratio of the base to the curing agent of from about 10:1 to about 20:1. A higher ratio may result in reproduction of greater details of surface of the leaf 80. To avoid excessive heating, which results in the leaves shriveling during curing, and consequently loss of fidelity of the imprint, the leaf imprints may be cured at a temperature from about 20° C. to about 25° C. for approximately 24-72 hours.

After curing, at step 102, the negative mold 90 is detached and the resulting surface replica is cut out from the negative mold 90 in the shape of the leaf 80 as shown in slides B and F of FIG. 3. At step 104, the negative mold 90 is used to form the replica of the leaf surface on top of the layer 20, i.e., uncured second layer, which is applied in the manner described above. In particular, the negative mold 90 is pressed onto the uncured layer 20 and then the layer 20 is cured with the negative mold 90 attached thereto as shown in slides C and G of FIG. 3. Curing may be done at a temperature of about 60° C. for approximately 24-48 hours. Prior to replicating the surface, the negative mold 90 may be functionalized with a fluorinated trichlorosilane, such as trichloro(1H,1H,2H,2H-perfluorooctyl)silane (PFOCTS), to minimize adhesion and facilitate the peel-off process. Deposition of PFOCTS may be performed via gas-phase evaporation in a desiccator from about 1 hour to about 2 hours.

After curing, the negative mold 90 is peeled from the layer 20 at step 106, which forms the LWS 10 with a sensing surface that is the exact replica of the chosen leaf as shown in slides D and H of FIG. 3. In embodiments, the layer 20 may be treated with an oxygen plasma to adjust (i.e., increase) the hydrophilicity of the polymer surface to more closely match the wettability of the leaves of interest. Oxygen plasma creates hydroxyl (OH) groups on the surface of the polymer that increase surface hydrophilicity. Hydroxyl groups on the polymer surface tend to have a lifetime of hours to days depending on conditions and the surface contact angle tends to plateau to an intermediate hydrophilicity. The layer 20 may also be formed from stable self-assembled monolayers on the to provide a long-term hydrophobicity.

During operation the LWS 10 is coupled to a datalogger via two leads, each of the leads being electrically coupled to the electrodes 16 and 18. The data logger may be any computing device having a single-ended analog input from the receive electrode 18 and one switched excitation channel for the transmit electrode. The data logger may calculate capacitance of the LWS 10 based on the received signals. The capacitance may then be used to calculate the leaf wetness since capacitance varies with the size (i.e., total contact surface area) of the droplets.

Accurate measurement of leaf wetness duration is essential to plant disease forecasting systems used to directly inform management practices, including the use of agrochemicals and timing of irrigation systems. Commercial leaf wetness sensors estimate the amount of surface water and leaf wetness duration by measuring the change in capacitance of a surface that accumulates condensed water. However, the one-size-fits-all commercial sensors do not accurately reflect the variation in leaf traits among species that dramatically affects leaf wetness duration. The present disclosure provides biomimetic leaf wetness sensors designed to closely replicate the physical and wettability properties of leaves of individual plant species. These sensors provide a more accurate measurement of leaf wetness duration than do currently available hydrophilic commercial sensors. Overestimating leaf wetness duration would erroneously elevate perceived risk of disease development, potentially leading to unnecessary application of fungicides with negative environmental and economic impacts. For crops with more hydrophilic leaves, underestimated leaf wetness could lead to missed opportunities to control disease. Custom-built LWS according to the present disclosure are inexpensive to produce—required materials cost about US $5 per sensor. The replica molding strategy disclosed herein is applicable to any type of leaf, and therefore is applicable to all crops, horticultural plants, or wild species that are the focus of monitoring or research. The LWSs accurately measure leaf wetness and can therefore improve disease forecasting and facilitate integrated pest management.

The following Examples illustrate embodiments of the present disclosure. These Examples are intended to be illustrative only and are not intended to limit the scope of the present disclosure.

Example 1

This Example describes PCB LWS design.

The PCB sensor interdigital electrode design was printed on a 1.6 mm thick fiberglass substrate and with the sensor head area constrained to approximately 20×45 mm² area. Each electrode had a finger width of about 1 mm and a gap space of 250 µm. The PCB electrode side was covered with a 25 µm protective coating of PDMS (10:1 weight ratio) by spin coating at 1,000 rpm for 10 min. The coated PCB sensor was then cured in an oven at a temperature of for 48 h.

Example 2

This Example describes leaf replica fabrication.

To create the negative mold, leaves were first removed from plants, rinsed under running water for one minute, and dried with nitrogen gas. Within a few hours of collection, the leaf was attached to a disposable Petri dish using double-sided Kapton tape. PDMS (SYLGARD 184; Dow Corning, USA) was prepared by mixing the PDMS prepolymer and cross linker in a 20:1 weight ratio and degassed for about 1 hour in a vacuum desiccator to remove air bubbles. The ratio PDMS was poured into the Petri dish containing the leaf; the Petri dish was then placed back into the vacuum desiccator to remove any further bubbles formed during the pouring process. The PDMS was cured in an oven in ambient air at a temperature of 25° C. for 72 h. Once fully cured, the PDMS negative mold replica was cut and peeled from the template.

Example 3

This Example describes assembly of LWS.

To imprint the PCB sensor with the leaf pattern, the negative leaf replica mold was pressed into the PCB sensor. A second layer of PDMS was spun at 250 rpm for 60 seconds to yield a 200 µm layer on the PCB sensor. Next, the negative mold leaf replica was treated with trichloro(1H,1H,2H,2H-perfluorooctyl)silane (PFOCTS) (97% Sigma Aldrich, USA) to act as a non-stick agent. Deposition of PFOCTS was performed via gas-phase evaporation in a desiccator for about 2 hours. The treated negative mold leaf replica was then firmly pressed face-down into the coated PCB sensor and was cured in an oven at a temperature of 60° C. for about 48 hours. Once fully cured, the negative leaf replica mold was peeled from the PCB sensor.

Example 4

This Example describes plasma treatment of assembled LWS.

Replica PDMS leaf surfaces were further treated following sensor assembly. After coating, replica LWS were exposed to oxygen plasma treatment at a base pressure of 40 mTorr, oxygen flow rate of 17.6 sccm, and RF plasma power of 45 W for exposure times varying between 10-60 seconds.

Example 5

This Example describes experimental leaf wetting setup.

Figure 4:
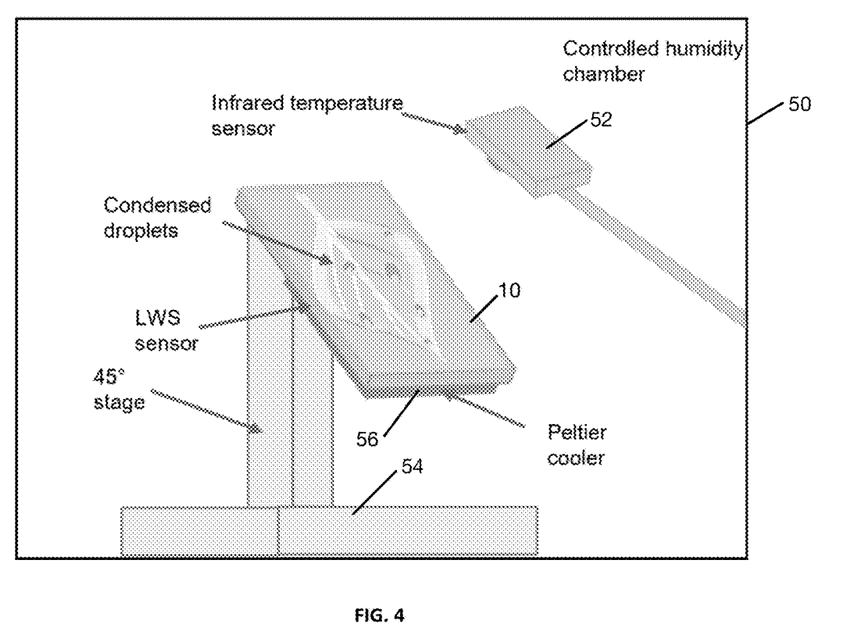
FIG. 4 is a schematic diagram of a chamber for measuring leaf wetness using LWS according to an embodiment of the present disclosure.

With reference to FIG. 4, artificial dew formation was performed in a controlled dew chamber 50, which allowed for regulation of meteorological factors including ambient temperature and humidity. A plurality of 80 mm fans were distributed around the chamber to facilitate the movement of air. Within the chamber 50, a relative humidity of 80% was maintained via a closed-loop system using an ultrasonic humidifier and a humidity sensor (not shown). Meteorological factors including ambient temperature and humidity were regulated using the DH22 humidity and temperature sensor (Adafruit, USA) and an ultrasonic mist maker (AGPTEK, USA). To induce condensation, the surface of the LWS was set to a temperature of 36° C. and controlled using a closed-loop system involving an infrared temperature sensor 52 and Peltier cooler. Each LWS was mounted at a 45° angle using a custom 3-D printed stage 54. Furthermore, a Peltier cooler 56 was mounted underneath to control the temperature inducing water droplet condensation. Recordings of the fabricated LWSs replicating the leaf surface of its corresponding leaf species were performed for a total of 30 minutes to reach full surface water saturation.

The subcooling of the sensor surface was controlled by setting the Peltier cooler 56 at a temperature of 36° C. However, temperature readings from the temperature sensor 52 recorded higher values compared to the Peltier set temperature owing to the thermal contact resistance of the 1.6 mm sensor substrate. To mediate this, a second closed-loop system involving an infrared camera and Peltier cooler 56 was used on each LWS. Recordings of the fabricated LWSs based on replicating the surface of its corresponding leaf species were performed. In addition, a LWS mimicking the wettability of the commercial LWS was also placed within the chamber 50.

Example 6

Figure 5:
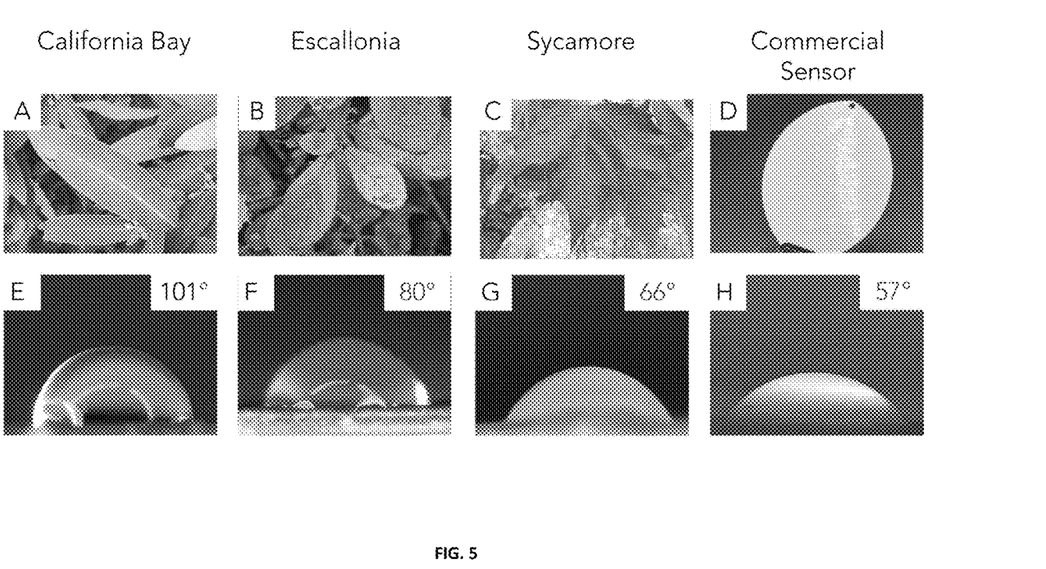
FIG. 5 shows photographs of leaves of California bay, *Escallonia* hybrid, and Western Sycamore, and a commercial LWS and corresponding photographs of water contact angles.
Figure 6:
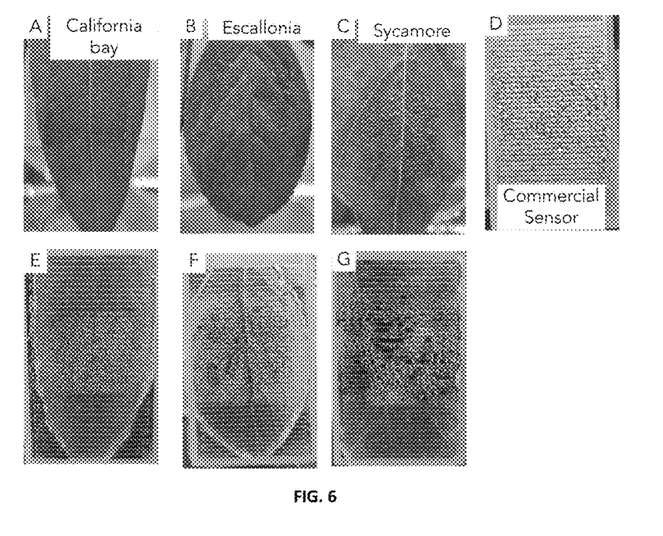
FIG. 6 are photographs of leaves and corresponding LWSs including replica surfaces and the commercial LWS.

This Example describes analysis of wettability of the LWSs according to the present disclosure and commercially available LWS.

leaves from three co-occurring plant species (California bay, sycamore, and *Escallonia*) that represent a range of leaf wettability (see slides A-C of FIG. 5) were used to form three replica surfaces for the biomimetic LWS as shown in slides E-G of FIG. 6, respectively. The biomimetic LWSs were compared the replica surfaces to the surface of the PHYTOS 31 (METER GROUP, USA) commercial sensor (slide D of FIG. 5 and slide D of FIG. 6). The wettability of the leaf surfaces was quantified by measuring the contact angle (θ) of a sessile water droplet.

Figure 7:
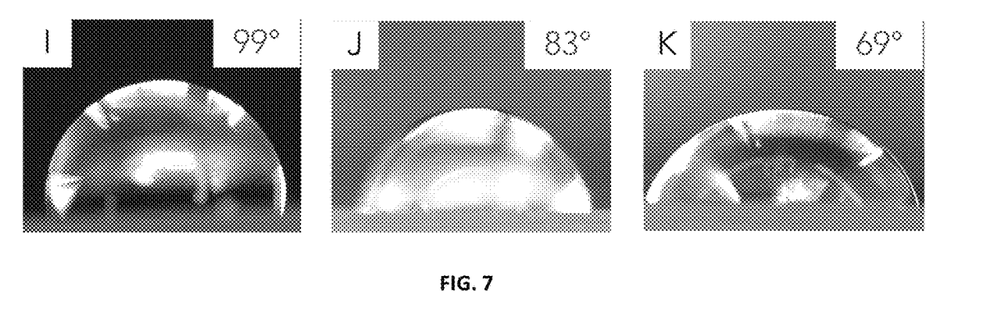
FIG. 7 shows water contact angles of surface layers of LWSs of FIG. 6 according to an embodiment of the present disclosure.

Contact angle measurements were obtained using a VHX-5000 Digital Microscope (Keyence, USA) and analyzed using Image J (imagej.nih.gov). Deionized water was used to determine the surface energy of leaves and PDMS leaf replicas. Contact angles were measured on water droplets with a volume of 5 μL. Measuring the contact angle of a sessile water droplet is a good predictor of how water will interact with and wet a surface and this measurement was used to compare the leaves and the replicas. The selected plant species include leaves that represent a range of hydrophobicity due to their leaf surface microstructure and surface chemistry. While none of the leaves that were selected had extreme superhydrophobic or superhydrophilic contact angles, they ranged from the hydrophobic California bay (θ=101° (slide E of FIG. 5), followed by the less hydrophobic *Escallonia* (θ=80° (slide F of FIG. 5), to the somewhat hydrophilic West Sycamore (θ=66° (slide G of FIG. 5). For comparison, the surface of the commercial sensor was more hydrophilic than any leaves tested (θ=57° (slide H of FIG. 5). As a result, when exposed to atmospheric moisture, the commercial sensor is likely to accumulate more water than the plant leaves and would retain the water longer. To confirm that the replica molding process creates a faithful replica of the target leaves, contact angles of the leaf replica were measured (see slides I-K of FIG. 7) to ensure that they were within 3° of the contact angle of the original leaves (see slides E-G of FIG. 5).

Figure 8:
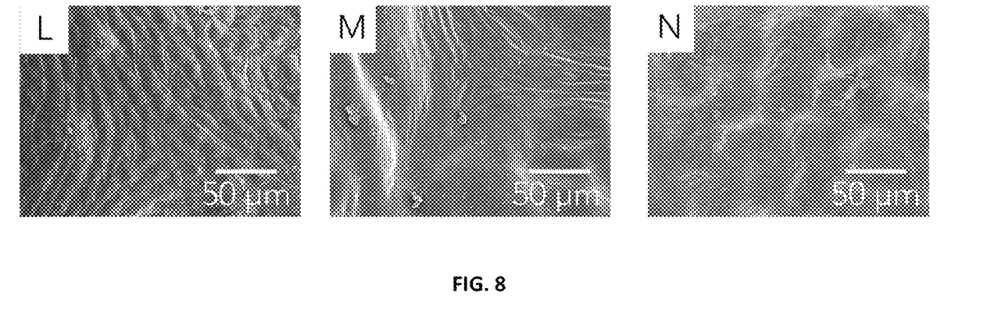
FIG. 8 are scanning electron microscope (SEM) images of the leaves of FIG. 5.
Figure 9:
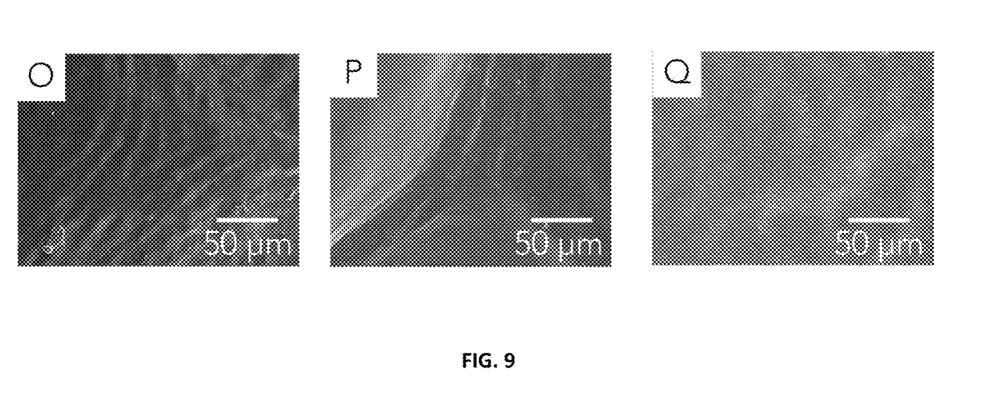
FIG. 9 are SEM images of the surface layers of LWSs of FIG. 6.

To further characterize the results of the replica molding process, we acquired Scanning electron microscope (SEM) images of the original leaves (slides L-N of FIG. 8) and the PDMS replicas, respectively (slides O-Q of FIG. 9). SEM images were taken using a FEI Quanta™ 3D field emission microscope (FEI, USA). Surfaces were observed at a power of 10 kV and spot size of 3.5 nm. As shown in the images, the replicas captured the important morphological traits of the leaf surfaces such as spacings of leaf cells and venation patterns. These patterns range from approximately 10 μm in the California bay leaf and replica (see slide L of FIG. 8 and slide O of FIG. 9) to approximately 40 μm in the Sycamore (see slide N of FIG. 8 and slide Q of FIG. 9). Thus, the disclosed method produced replicas of high quality and appropriate for use with LWS because their contact angle and wettability were the same as the contact angle and wettability of the original leaves.

To test whether the replica of the leaves would mimic the wetting behavior of the real leaves, condensation behavior of water droplets generated in a custom-made humidity and dew-controlled chamber of Example 5. After 30 minutes in the chamber, the same wetting patterns appeared on the leaves (slides A-C of FIG. 6) and their corresponding replicas (slides E-G of FIG. 6). The commercial sensor (slide D of FIG. 6) showed more surface condensation than any of the leaves, as expected based on its greater hydrophilicity (contact angle 57°). These patterns were expected because the amount of water condensation and retention depends on the physiochemical characteristics of the condenser surface of the leaves and the replicas. Therefore, leaves and replicas with lower contact angle are expected to condense and accumulate larger quantities of water than their more hydrophobic counterparts with higher contact angle.

Figure 10:
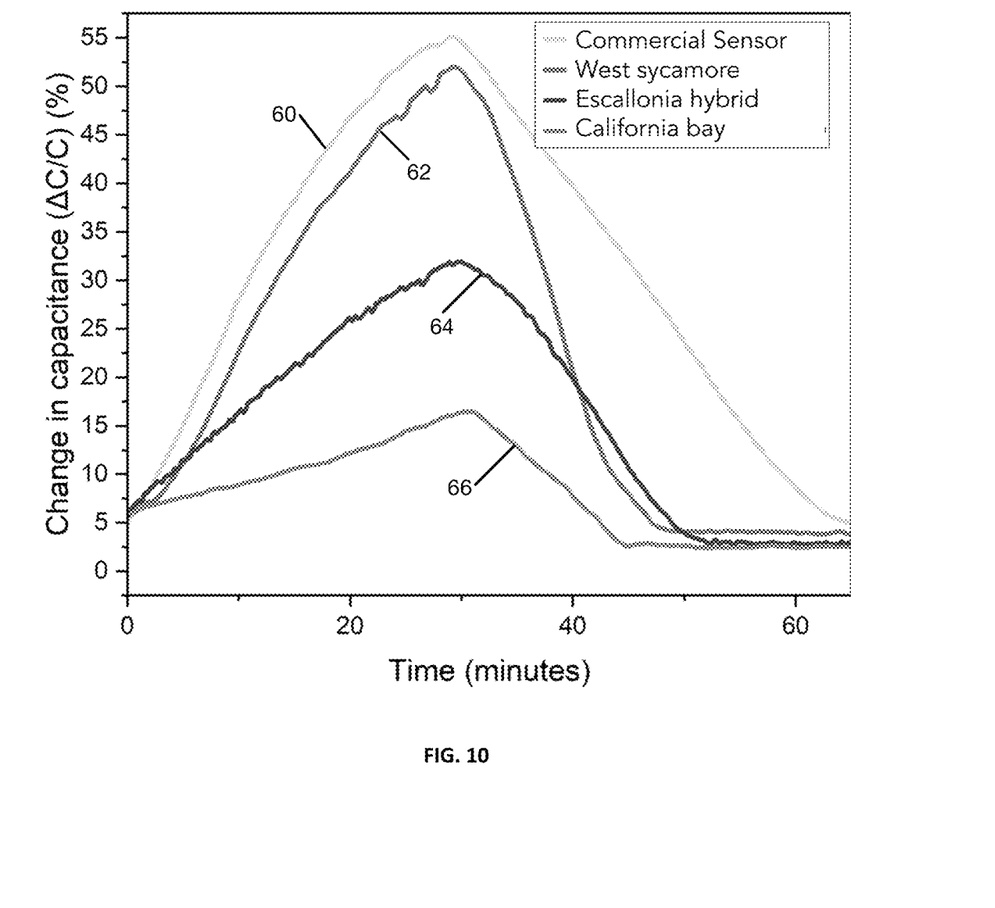
FIG. 10 shows plots of change in capacitance as a function of time of the LWSs of FIG. 6.

Measurements of the sensor capacitance acquired over 70 minutes are shown as plots in FIG. 10. Capacitance measurements were taken using the PCAP02 Capacitance-to-Digital Converter (ScioSense, The Netherlands). Plots 60, 62, 64, 66 show the capacitance plots for the commercial sensor, west sycamore LWS, *Escallonia* LWS, and the California bay LWS, respectively. The plots mirror the visible patterns of wetting in the images of FIG. 9, in which slides A-C show wetting pattens on California bay, *Escallonia*, and sycamore leaves and slides E-G show wetting pattens on their corresponding LWSs, with slide D showing the wetting pattern on the commercial sensor. This was consistent with expectations because the change in sensor capacitance is a function of the amount of water condensed and accumulated on the sensor. Therefore, sensors with more wettable surfaces record greater change in capacitance (ΔC). As expected, the hydrophilic commercial sensor (θ=57° captured a film of condensed water and yielded the greatest change in capacitance (see slide D of FIG. 9 and plot 60 of FIG. 10). After minutes, the commercial sensor (θ=57° exhibited a ΔC of 55%, higher than the moderately hydrophilic sycamore replica sensor (θ=69°; ΔC=52%), the moderately hydrophobic *Escallonia* replica sensor (θ=83°; ΔC=32%), and the hydrophobic bay replica sensor (θ=99°; ΔC=9%). These trends were reflected in the close correlation between θ (a measure of the surface relative surface free energy) and sensor capacitance response (ΔC) (Pearson's r=−0.974). With both the commercial sensor and sycamore leaves being hydrophilic, the commercial sensor could provide appropriate estimates of leaf wetness for that species; however, the commercial sensor would overestimate leaf wetness for the more hydrophobic species by as much as 50% as shown by the plots 60-64 of FIG. 10. The sensors appeared to be stable to prolonged wetting. There was no observable swelling or change in transparency of the replica sensors that would indicate excessive water absorption and an associated change in surface properties. These measurements indicate that hydrophilicity and hydrophobicity of the leaf and sensor surfaces affect both water condensation and accumulation as well as recorded change in capacitance of the sensor. The measurements also confirm that a sensor with surface properties closer to the leaf of interest accurately records water condensation and accumulation than a generic sensor since the replica molded surfaces reflect water affinity of the leaves.

It will be appreciated that of the above-disclosed and other features and functions, or alternatives thereof, may be desirably combined into many other different systems or applications. Also, various presently unforeseen or unanticipated alternatives, modifications, variations, or improvements therein may be subsequently made by those skilled in the art which are also intended to be encompassed by the following claims. Unless specifically recited in a claim, steps, or components according to claims should not be implied or imported from the specification or any other claims as to any particular order, number, position, size, shape, angle, or material.

What is claimed is:

1. A biomimetic leaf wetness sensor comprising:
    a capacitive sensor; and
    a non-conductive polymer layer disposed over the capacitive sensor, the layer having a replica molded surface corresponding to a plant leaf.

2. The biomimetic leaf wetness sensor according to claim 1, wherein the capacitive sensor includes:
    a substrate;
    a first interdigital electrode having a plurality of first digits disposed on the substrate; and
    a second interdigital electrode having a plurality of second digits disposed on the substrate, wherein the plurality of first digits and the plurality of second digits are interdigitated.

3. The biomimetic leaf wetness sensor according to claim 2, wherein each digit of the plurality of first digits and the plurality of second digits has a width from about 500 μm to about 1,500 μm.

4. The biomimetic leaf wetness sensor according to claim 2, wherein the plurality of first digits and the plurality of second digits are separated by a gap from about 250 μm to about 1500 μm.

5. The biomimetic leaf wetness sensor according to claim 1, wherein the non-conductive polymer layer has a thickness from about 100 μm to about 300 μm.

6. The biomimetic leaf wetness sensor according to claim 1, wherein the non-conductive polymer layer is treated with an oxygen plasma to increase hydrophilicity.

7. The biomimetic leaf wetness sensor according to claim 1, wherein the non-conductive polymer layer is formed from polydimethylsiloxane.

8. The biomimetic leaf wetness sensor according to claim 1, wherein the replica molded surface is formed by placing a replica mold of the plant leaf onto the non-conductive polymer layer during curing thereof.

9. A biomimetic leaf wetness sensor comprising:
an interdigital capacitive sensor; and
a polysiloxane layer disposed over the capacitive sensor, the layer having a replica molded surface corresponding to a plant leaf.

10. The biomimetic leaf wetness sensor according to claim 9, wherein the polysiloxane layer has a thickness from about 100 μm to about 300 μm.

11. The biomimetic leaf wetness sensor according to claim 9, wherein the polysiloxane layer is treated with an oxygen plasma to increase hydrophilicity.

12. The biomimetic leaf wetness sensor according to claim 9, wherein the replica molded surface is formed by placing a replica mold of the plant leaf onto the non-conductive polymer layer during curing thereof.

* * * * *